US010190573B2

(12) United States Patent
Lee

(10) Patent No.: US 10,190,573 B2
(45) Date of Patent: Jan. 29, 2019

(54) BLADE CONTROL APPARATUS AND METHOD FOR WIND POWER GENERATOR, AND WIND POWER GENERATOR USING THE SAME

(71) Applicant: DOOSAN HEAVY INDUSTRIES & CONSTRUCTION CO., LTD., Changwon-si (KR)

(72) Inventor: Sang Il Lee, Dong-gu (KR)

(73) Assignee: Doosan Heavy Industries Construction Co., Ltd, Gyeongsangnam-do (KR)

(*) Notice: Subject to any disclaimer, the term of this patent is extended or adjusted under 35 U.S.C. 154(b) by 343 days.

(21) Appl. No.: 14/588,665

(22) Filed: Jan. 2, 2015

(65) Prior Publication Data
US 2015/0184636 A1    Jul. 2, 2015

(30) Foreign Application Priority Data

Jan. 2, 2014    (KR) .................. 10-2014-0000355

(51) Int. Cl.
F03D 7/04    (2006.01)
F03D 9/25    (2016.01)
(Continued)

(52) U.S. Cl.
CPC ........... F03D 7/042 (2013.01); F03D 1/0675 (2013.01); F03D 7/02 (2013.01); F03D 7/048 (2013.01);
(Continued)

(58) Field of Classification Search
CPC ........ F03D 3/062; F03D 7/0204; F03D 7/042; F03D 7/0224; F03D 7/0244;
(Continued)

(56) References Cited

U.S. PATENT DOCUMENTS 6,940,186 B2 * 9/2005 Weitkamp .............. F03D 7/042
290/44
7,494,324 B2 * 2/2009 Hibbard ................. H02G 13/00
416/226

(Continued)

FOREIGN PATENT DOCUMENTS

EP    2 314 866 A1    4/2011
JP    2013-148022 A    8/2013
JP    2013148022 A    8/2013

OTHER PUBLICATIONS

Korean Office Action dated Dec. 24, 2015, issued in corresponding Korean Patent Application No. 10-2014-0000355.
(Continued)

Primary Examiner — Carlos A Rivera
Assistant Examiner — Eric Zamora Alvarez
(74) Attorney, Agent, or Firm — Invenstone Patent, LLC

(57) ABSTRACT

The present invention relates to a blade control apparatus and method for a wind power generator, and a wind power generator using the same, which includes a measurement unit configured to measure a change in electrical characteristic of a measurement section set in a conductive region having electrical conductivity. The conductive region is included in the blade for the wind power generator. Thus, the state of the blade may be easily checked without separate sensors, and the blade may be controlled in response to the state of the blade.

16 Claims, 9 Drawing Sheets

(51) Int. Cl.
*F03D 17/00* (2016.01)
*F03D 1/06* (2006.01)
*F03D 7/02* (2006.01)
*G01N 27/20* (2006.01)

(52) U.S. Cl.
CPC .............. *F03D 9/257* (2017.02); *F03D 17/00* (2016.05); *G01N 27/20* (2013.01); *F05B 2240/30* (2013.01); *F05B 2280/2006* (2013.01); *F05B 2280/6013* (2013.01); *Y02E 10/721* (2013.01); *Y02E 10/723* (2013.01)

(58) Field of Classification Search
CPC ........ F03D 7/0264; F03D 80/00; F03D 80/30; F03D 80/40; F03D 80/50; F03D 1/065
See application file for complete search history.

(56) References Cited

U.S. PATENT DOCUMENTS

| | | | |
|---|---|---|---|
| 7,503,752 B2 * | 3/2009 | Gunneskov | F03D 1/065 416/229 R |
| 7,569,944 B2 * | 8/2009 | Oohara | F03D 7/0224 290/44 |
| 7,594,797 B2 * | 9/2009 | Wobben | F03D 17/00 416/61 |
| 7,883,319 B2 * | 2/2011 | Volkmer | F03D 17/00 416/146 R |
| 7,921,727 B2 * | 4/2011 | Rice | G01B 7/18 73/762 |
| 8,170,810 B2 * | 5/2012 | Volkmer | F03D 7/0224 290/44 |
| 8,255,173 B2 * | 8/2012 | Fujioka | F03D 17/00 290/44 |
| 8,714,912 B2 * | 5/2014 | Gierlich | F03D 17/00 415/118 |
| 2006/0133933 A1 | 6/2006 | Wobben | |
| 2009/0277266 A1 * | 11/2009 | Wang | F03D 7/0224 73/514.01 |
| 2011/0044820 A1 * | 2/2011 | Stenbaek Nielsen | B29C 70/342 416/223 R |
| 2013/0035878 A1 * | 2/2013 | Wesby | F03D 7/042 702/42 |

OTHER PUBLICATIONS

Communication dated May 21, 2015 from the European Patent Office in counterpart application No. 14191928.2.

* cited by examiner

BLADE CONTROL APPARATUS AND METHOD FOR WIND POWER GENERATOR, AND WIND POWER GENERATOR USING THE SAME

CROSS-REFERENCE(S) TO RELATED APPLICATIONS

This application claims priority to Korean Patent Application No. 10-2014-0000355, filed on Jan. 2, 2014, the disclosure of which is incorporated herein by reference in its entirety.

BACKGROUND OF THE INVENTION

Field of the Invention

Exemplary embodiments of the present invention relate to a blade control apparatus and method for a wind power generator, and a wind power generator using the same, and more particularly, to a blade control apparatus and method for a wind power generator, which measures the change in electrical characteristic of a member forming a blade so as to control the blade, and a wind power generator using the same.

Description of the Related Art

A wind power generator refers to a power generator which generates power using wind power which is natural energy. The wind power generator generates electricity by converting wind power into a mechanical rotational force, and includes a blade, a nacelle, and a tower.

The wind power generator generates a rotational force based on an aeromechanical lift force of the blade which acts against wind blowing from the front. The rotation of the blade changes the aerodynamic load distribution around the blade, and the change of the aerodynamic load distribution is applied as a bending load or twisting load to the blade.

The blade may be damaged by the application of such a load and the surrounding environment condition such as rainfall, corrosion caused by salt contained in seawater, or collision with foreign matters in the air. In this case, deformation, deterioration, or delamination may occur inside and outside the blade.

According to a conventional method, an operator checks the state of a blade with the naked eye, when a wind power generator is regularly inspected, or when the rotation of the blade is stopped. Then, the operator repairs the blade, changes the operation condition, or replaces a part in response to the state information of the blade, which is analyzed through the checking operation.

In such a method, however, the state of the blade can be checked only in a state where the blade is stopped, and the operator must check the state of the blade with the naked eye.

In order to solve such a problem, various techniques have been proposed to determine whether a blade for a wind power generator is damaged.

For example, a measurement unit such as an optical fiber sensor or strain gauge may be used to check the state of a blade, and the blade may be controlled according to the state of the blade.

As a specific example of an apparatus for detecting the state of a blade, Korean Patent Laid-open Publication No. 10-2013-0052965 has disclosed a physical quantity sensing apparatus of a wind turbine blade.

The disclosure relates to a physical quality sensing apparatus of a wind turbine blade, which includes optical fiber for totally reflecting light incident from a light source and a Bragg grating for sensing a physical quantity of a blade for wind power generation by reflecting light at a Bragg wavelength range in the light transmitted through the optical fiber.

The apparatus according to the above-described disclosure includes a required number of optical fiber Bragg grating sensors and temperature-compensated Bragg grating sensors which are attached at the top or bottom of a shear web, and senses the temperature, the strain rate, and the deflection of the blade through the sensors.

However, since the optical sensors or strain gauges are expensive and difficult to deal with, only a skilled engineer can install the optical sensors or strain gauges. Furthermore, since the optical sensors or strain gauges are vulnerable to vibration, the optical sensors or strain gauges may frequently break down after installation. Thus, there are difficulties in managing and repairing the optical sensors or strain gauges.

Furthermore, since the optical sensors or strain gauges are sensitive to temperature change, a process of removing a change caused by temperature effect using data processing technology must be accompanied. The process is technically difficult to perform, and requires a compensation process. Thus, it is difficult to secure the reliability of acquired information.

In particular, the measurement units can sense external deformation of the blade, such as deflection, but cannot sense internal damage. Therefore, the measurement units have limitation in availability.

SUMMARY OF THE INVENTION

The present invention has been made in view of the above problems, and it is an object of the present invention to provide a blade control apparatus and method for a wind power generator, which controls a blade using a blade state measurement unit provided at a low cost and capable of securing the reliability of measured information, and a wind power generator using the same.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with one aspect of the present invention, there is provided a blade control apparatus which determines the state of a blade for a wind power generator, having a conductive region formed of carbon fiber, and controls a rotation condition of the blade. The blade control apparatus may include: a measurement unit configured to measure an electrical characteristic of a measurement section set in the conductive region; a determination unit configured to compare the value measured through the measurement unit to a reference value and determine whether the blade is in a normal state or emergency state; and a control unit configured to set a mode to any one of a normal mode, an abnormal mode, and a stop mode in response to the state determined by the determination unit, and control the rotation condition of the blade according to the set mode.

The measurement section may include a plurality of sections set in the conductive region.

The measurement unit may repetitively measure the electrical characteristic of the measurement section.

The measurement unit may determine a level based on a difference between the measured value and the reference value, when determining the level of the emergency state.

The control unit may transmit a rotation speed control signal for the blade in response to the level of the emergency state determined by the determination unit.

The control unit may transmit a stop control signal for the blade in response to the level of the emergency state determined by the determination unit.

The control unit may transmit a pitch control signal for the blade in response to the level of the emergency state determined by the determination unit.

The control unit may transmit a yaw control signal in response to the level of the emergency state determined by the determination unit.

The control unit may the set mode information to an eternal terminal.

The control unit may transmit the set mode information as an e-mail or text message or transmit the set mode information to the external terminal such that the mode information is displayed on a display screen of the external terminal.

The control unit may transmit a control signal to a warning light or warning sound generator, when the determination unit determines that the blade is in an emergency state.

In accordance with another aspect of the present invention, there is provided a wind power generator including a blade having a conductive region. The wind power generator may include a measurement unit configured to measure a change in electrical characteristic of a measurement section set in the conductive region.

The conductive region may include a carbon fiber member and thus has electrical conductivity.

The measurement section may include one section or a plurality of sections set in the conductive region.

The blade may include a skin, a spar cap, and a shear web, and the conductive region may be formed in one or more of the skin, the spar cap, and the shear web.

One or more of the skin, the spar cap, and the shear web may include a carbon fiber material and thus have the conductive region formed therein.

The conductive region may be formed across the skin and the spar cap, while including a connection part between the skin and the spar cap, and the measurement section may be set across the skin and the spar cap.

The conductive region may be formed across the spar cap and the shear web, while including a connection part between the spar cap and the shear web, and the measurement section may be set across the spar cap and the shear web.

Any one of the skin, the spar cap, and the shear web may be formed of a non-conductive member including glass fiber, and a conductor including carbon fiber may be formed in the non-conductive member so as to form the conductive region.

The conductor may include a carbon fiber material.

The measurement unit may be electrically connected to both ends of the measurement section so as to measure the electrical characteristic of the measurement section.

The measurement unit may repetitively measure the electrical characteristic of the measurement section.

The wind power generator may further include a determination unit configured to compare the value measured through the measurement unit to a reference value, and determine whether the blade is in a normal state or emergency state.

The determination unit may determine a level based on a difference between the measured value and the reference value, when determining the level of the emergency state.

The wind power generator may further include a control unit configured to set a mode to any one of a normal mode, an abnormal mode, and a stop mode in response to the state determined by the determination unit, and control the blade according to the set mode.

The control unit may transmit a rotation speed control signal in response to the level of the emergency state determined by the determination unit.

The control unit may transmit a stop control signal in response to the level of the emergency state determined by the determination unit.

The control unit may transmit a pitch control signal in response to the level of the emergency state determined by the determination unit.

The control unit may transmit a yaw control signal for the blade in response to the level of the emergency state determined by the determination unit.

The control unit may the set mode information to an eternal terminal.

The control unit may transmit the set mode information as an e-mail or text message or transmit the set mode information to the external terminal such that the mode information is displayed on a display screen of the external terminal.

The control unit may transmit a control signal to a warning light or warning sound generator, when the determination unit determines that the blade is in an emergency state.

In accordance with another aspect of the present invention, there is provided a blade control method which measures the state of a blade for a wind power generator, having a conductive region formed of carbon fiber, and controls a rotation condition of the blade. The blade control method may include operations of: measuring an electrical characteristic of a measurement section set in the conductive region; comparing the value measured at the measuring operation to a reference value and determining whether the blade is in a normal state or emergency state; setting a mode to any one of a normal mode, an abnormal mode, and a stop mode in response to the determined state determined at the comparing operation; and controlling the rotation condition of the blade according to the mode set at the setting operation.

The measuring operation may include measuring electrical characteristics of a plurality of measurement sections set in the conductive region.

The measuring operation may include repetitively measuring the electrical characteristic of the measurement section.

The comparing operation may include determining a level based on a difference between the measured value and the reference value, when determining the level of the emergency state.

The controlling operation may include controlling rotation speed of the blade in response to the level of the emergency state determined at the comparing operation.

The controlling operation may include stopping the blade in response to the level of the emergency state determined at the comparing operation.

The controlling operation may include controlling pitch of the blade in response to the level of the emergency state determined at the comparing operation.

The controlling operation may include performing yaw control for the blade in response to the level of the emergency state determined at the comparing operation.

The blade control method may further include an operation of checking generation quantity of the wind power generator after the controlling operation.

The wind power generator including the blade may be one of a plurality of wind power generators forming a wind farm, and the wind farm may include an integrated controller for controlling the plurality of wind power generators. The blade control method may further include an operation of transmitting the power generation information to the integrated controller after the checking operation.

The blade control method may further include an operation of transmitting the set mode information to an external terminal after the setting operation.

The transmitting operation may include transmitting the set mode information as an e-mail or text message or transmitting the set mode information to the external terminal such that the set mode information is displayed on a display screen of the external terminal.

The blade control method may further include an operation of turning on a warning light or generating a warning sound when it is determined at the comparing operation that the blade is in an emergency state, after the comparing operation.

The blade may include a skin, a spar cap connected to the skin, and a shear web connected to the spar cap, and the conductive region may be formed in one or more of the skin, the spar cap, and the shear web.

The conductive region may be formed across the skin and the spar cap, while including a connection part between the skin and the spar cap, and the measurement section may be set across the skin and the spar cap.

The conductive region may be formed across the spar cap and the shear web, while including a connection part between the spar cap and the shear web, and the measurement section may be set across the spar cap and the shear web.

It is to be understood that both the foregoing general description and the following detailed description of the present invention are exemplary and explanatory and are intended to provide further explanation of the invention as claimed.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF SPECIFIC EMBODIMENTS

Figure 1:
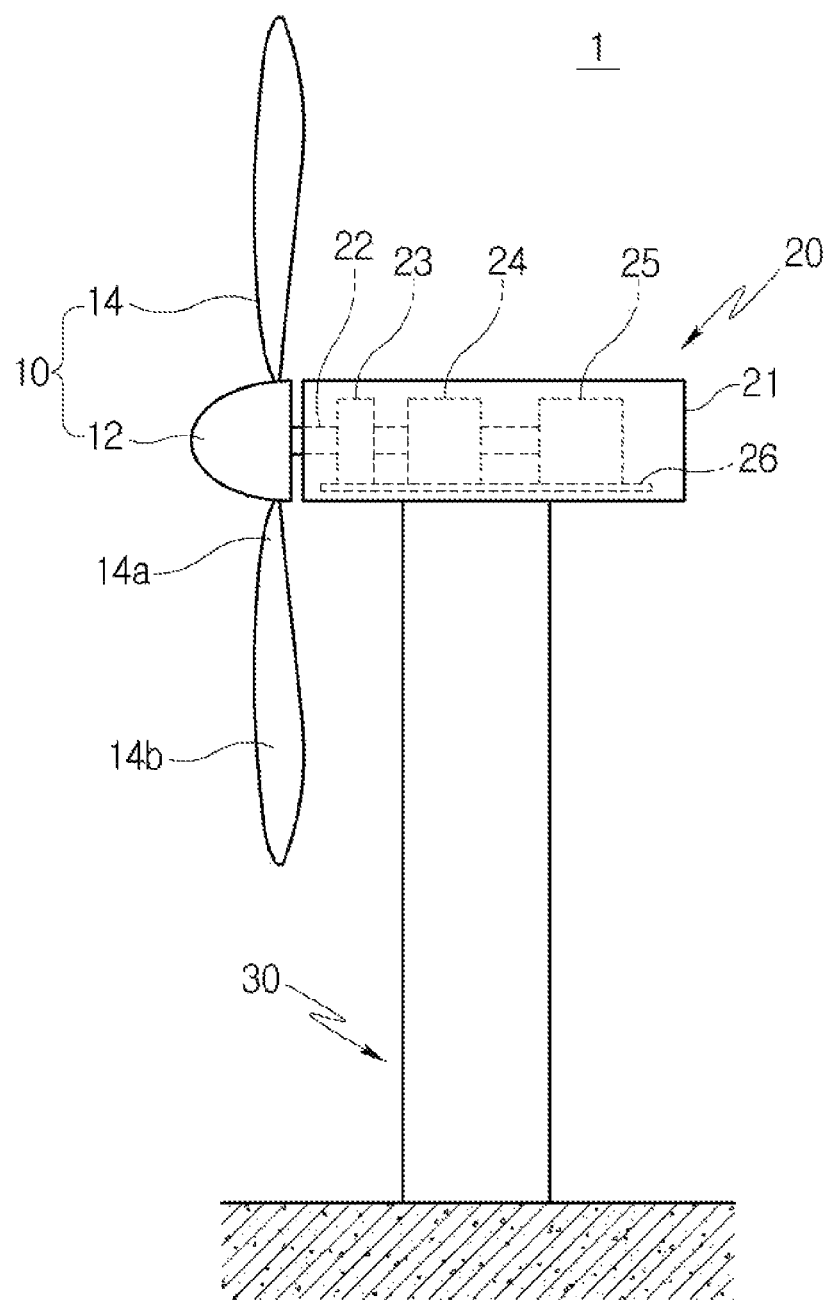
FIG. 1 is a schematic view of a wind power generator according to an embodiment of the present invention.

Hereinafter, an apparatus and method for controlling a blade for a wind power generator and a wind power generator using the same according to exemplary embodiments of the present invention will be described below in more detail with reference to the accompanying drawings.

In the drawings, the thicknesses of lines or the sizes of components may be exaggerated for clarity.

Furthermore, terms to be described are defined in considerations of functions in the present invention, and may differ depending on the intention or custom of a user or operator. Thus, the definition of the terms will be based on the overall contents of the present specification.

The following embodiments may not limit the scope of the present invention, but are only examples of components described in claims of the present invention. Thus, embodiments including components which are included in the spirit of the present specification and may be replaced with equivalents to components of claims may be included in the scope of the present invention.

Figure 2A:
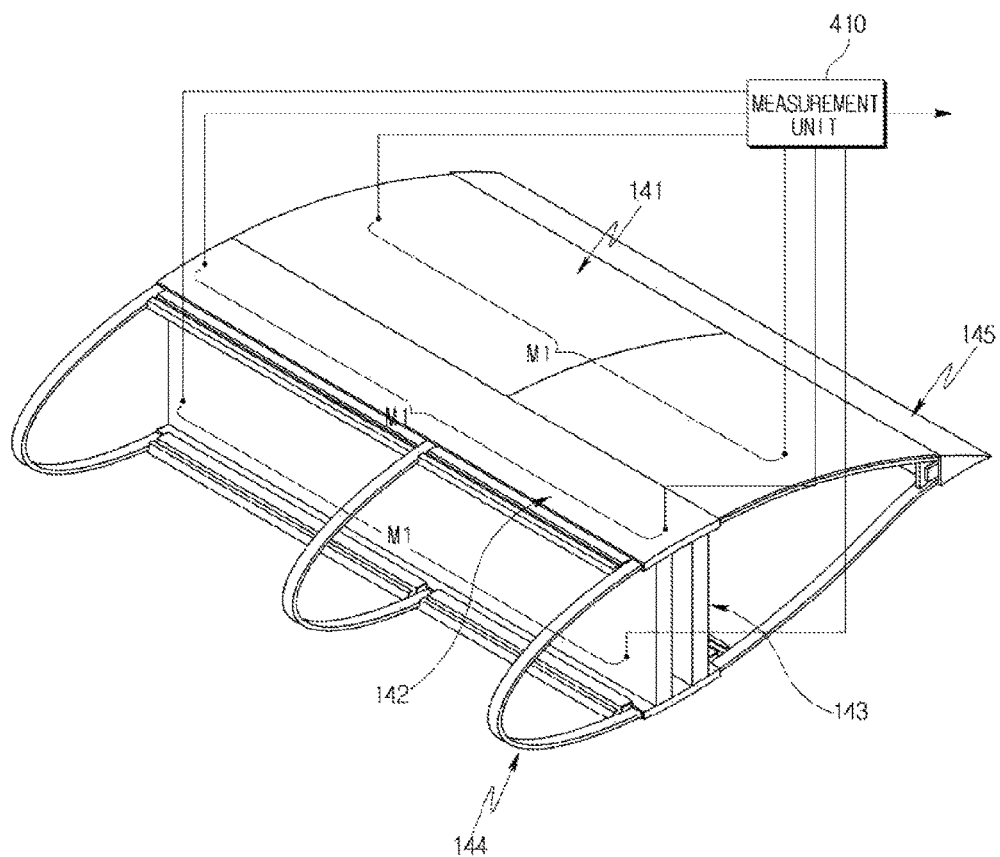
FIGS. 2A, 2B and 3 are diagrams illustrating the structure of a blade of FIG. 1.
Figure 2B:
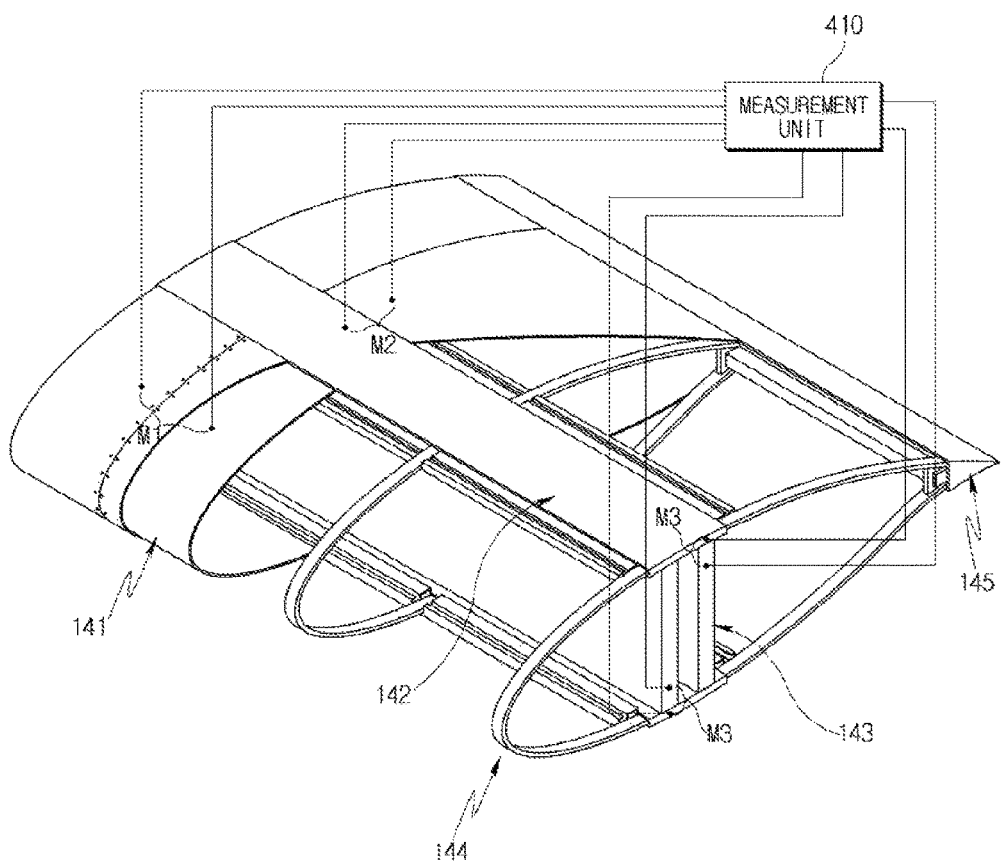
Figure 3:
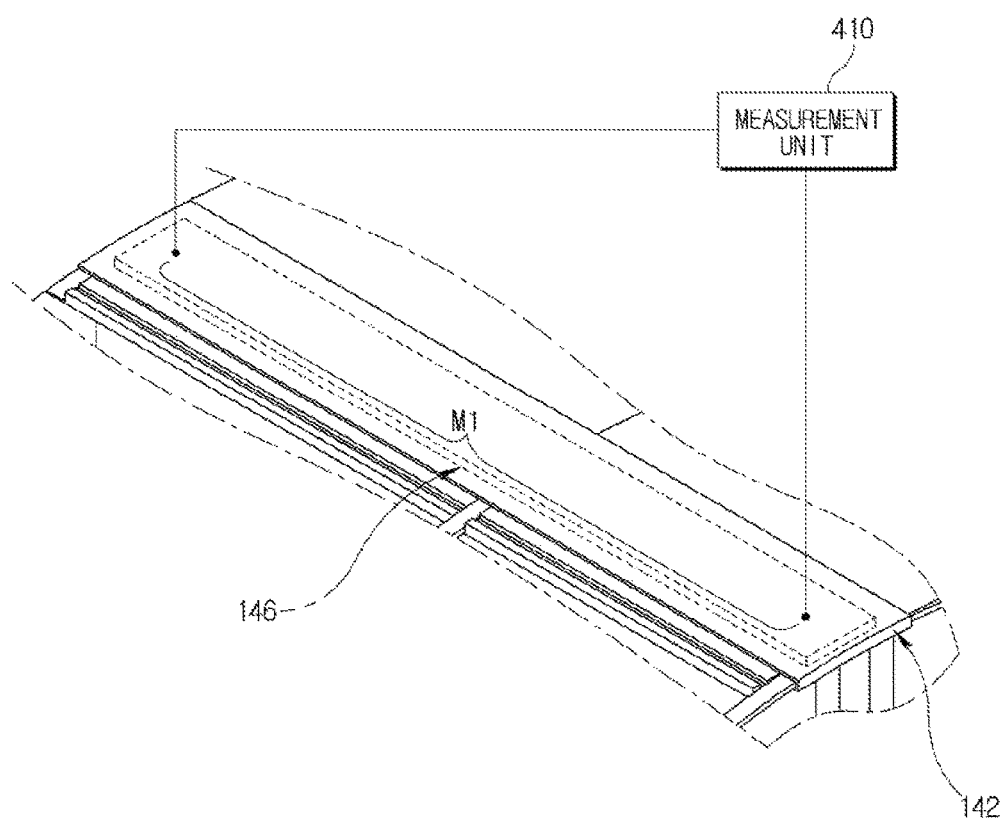
Figure 4:
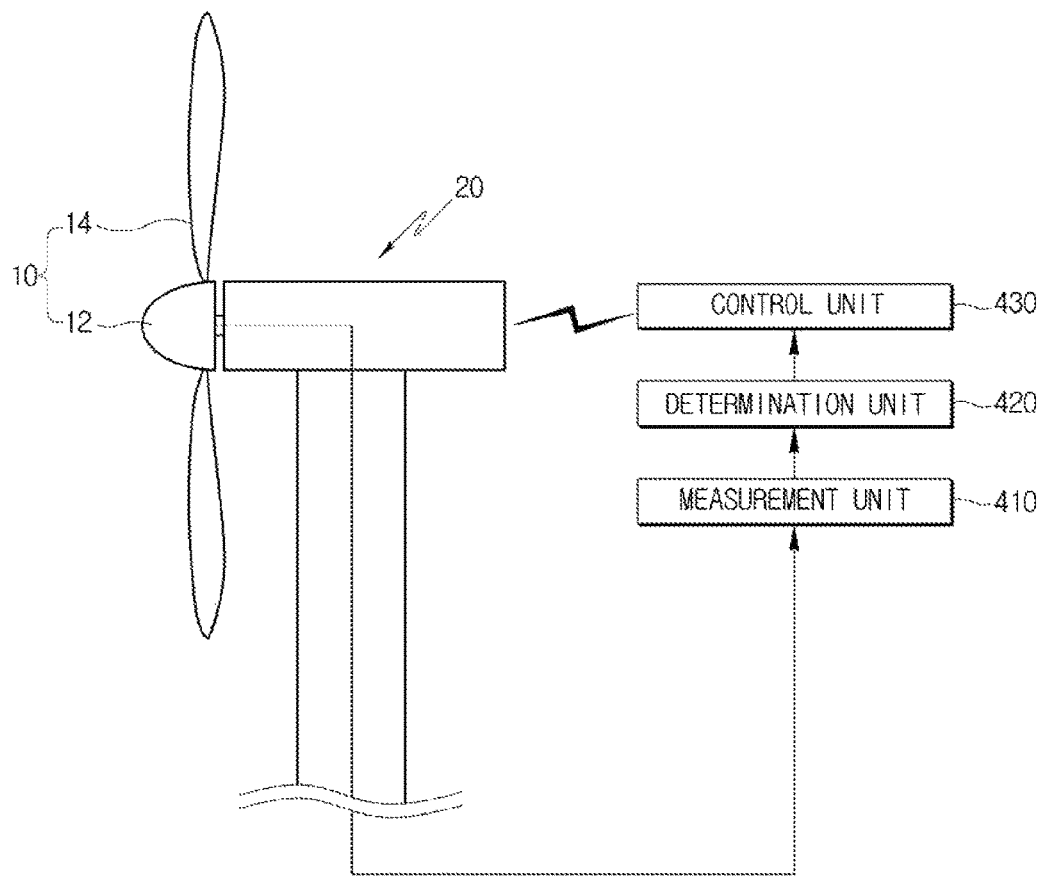
FIG. 4 is a schematic view of a blade control apparatus according to an embodiment of the present invention.

Hereafter, a wind power generator according to an embodiment of the present invention will be described with reference to FIGS. 1 to 4. FIG. 1 is a schematic view of a wind power generator according to an embodiment of the present invention. FIGS. 2A, 2B and 3 are diagrams illustrating the structure of a blade of FIG. 1. FIG. 4 is a schematic view of a blade control apparatus according to an embodiment of the present invention.

As illustrated in FIG. 1, the wind power generator 1 according to an embodiment of the present invention basically includes a rotor 10, a nacelle 20, and a tower 30.

The rotor 10 includes a hub 12 and a blade 14. The hub 12 is positioned at the front of the nacelle 20, and coupled to a main shaft 22. The hub 12 may have a hollow structure, and a pitch controller and a lubrication controller may be provided in the hub 12.

The blade 14 may include one or more blades. The blades 14 are arranged radially around the hub 12 in a state where root parts 14a thereof are coupled to the hub 12. The blade 14 may include a tip part 14b having a small cross-sectional area than the root part 14a.

As illustrated in FIGS. 2A and 2B, the blade 14 may have a wing-shaped cross-section. The blade 14 is coupled to the hub 12 so as to have an angle of attack with respect to wind blowing from the front. The wind blowing from the front of the wind power generator 1 generates a lift force while grazing the surface of the blade 14, and the generated lift force rotates the rotor 10. The rotational force of the rotor 10 is transmitted to the nacelle 20 and converted into electric energy.

The nacelle 20 may be rotatably supported by the tower 30. The nacelle 20 may include a nacelle cover 21, a main shaft 22, a bearing 23, a gear box 24, a generator 25, and a main frame 26 therein.

The nacelle cover 21 may be rotatably coupled to the top of the tower 340, and house the main shaft 22, the bearing 23, the gear box 24, the generator 25, and the main frame 26. The nacelle cover 21 may be formed of a non-conductive material, for example, fiber reinforced plastics (FRP).

The main shaft 22 is rotatably supported by the bearing 23, connects the hub 12 and the gear box 24, and transmits rotational energy of the hub 12 to the gear box 24 while rotating with the hub 12.

The gear box 24 increases the rotation speed inputted from the main shaft 22 to a speed for power generation, and outputs and transmits the rotational energy to the generator 25. The generator 25 converts the rotational energy outputted from the gear box 24 into electrical energy.

The tower 30 may have a hollow cylindrical shape, and supports the nacelle 20. Between the nacelle 20 and the tower 30, a yaw controller may be provided to rotate the nacelle 20 such that the rotor 10 faces or does not face the direction in which wind blows.

FIGS. 2A and 2B illustrate an example of the structure of the blade 14. As illustrated in FIGS. 2A and 2B, the blade 14 may include a frame 144, a skin 141, a spar cap 142, a shear web 143, and an edge part 145. The skin 141 is formed to tightly cover the frame 144, and forms the exterior of the blade 14. The spar cap 142 is coupled to the frame 144 and serves as a stiffener in the longitudinal direction. The shear web 143 is coupled to the spar cap 142 and serves as a stiffener in the thickness direction. The edge part 145 is coupled to an edge of the frame 144.

The structure of the blade 14 is not limited to the above-described example. The blade 14 may basically include the skin 141 and the spar cap 142, and additionally include the shear web 143. The frame 144 or the edge part 145 may be included or omitted, and another member forming the blade 14 may be further included in addition to the above-described components.

The blade for a wind power generator may be formed of FRP. The fiber used for the blade may include ceramic-based fiber such as glass or carbon fiber.

Until recently, glass FRP (GFRP) based on glass fiber has been mainly used. However, the radius of rotation of a blade has been increased annually in order to improve the efficiency of a wind power generation system. Furthermore, the efficiency has been degraded due to the weight of the blade, and the installation cost has significantly increased. Thus, the use of carbon fiber replacing glass fiber has gradually increased.

Carbon fiber has a larger specific strength than glass fiber. Thus, when a large-size blade is manufactured using carbon fiber, the weight of the blade may be reduced in comparison to a blade formed of glass fiber, while the stiffness of the blade is maintained. Therefore, carbon fiber contributes greatly to increasing the efficiency of the wind power generation system.

At least a part of the components forming the blade 14 may include a fiber material as described above.

For example, the spar cap 142 may be formed of a stacked body which includes glass fiber, carbon fiber, and/or other fibers on a base material made of proper thermosetting and/or thermoplastic resin. The shear web 143 may also be formed of a stacked body including glass fiber or carbon fiber. Furthermore, the skin 141 may have a sandwich structure including glass fiber or carbon glass.

Carbon fiber is a carbon material having a fiber length at which the mass content ratio of carbon element is equal to or more than 90%, and indicates fiber obtained by pyrolyzing polyacrylonitrile (PAN), pitch (asphalt) corresponding to petroleum/coal-based hydrocarbon residue, or a fiber-shaped organic precursor made from rayon in an inert atmosphere.

Carbon fiber is a material which has the structure of a carbon material in an organizing element and exhibits structural characteristics and fiber-type characteristics. Thus, carbon fiber includes excellent features such as thermal resistance, chemical stability, electrical stability, dimensional stability based on low thermal expansion, low density, abrasion friction, and flexibility.

The blade is a core part of a wind power generator. With the increase in size of wind power generators, the blade occupies a large part in terms of price or weight. Thus, the maintenance of the blade is becoming more and more important. Thus, the state of the blade needs to be continuously monitored.

Since the blade is affected by its own weight or surrounding environment conditions during operation, loads may be applied inside and outside the blade, pollutants may adhere to the blade, or icing may occur on the blade. The icing refers to a phenomenon in which ice is formed on a part of the blade under a specific condition, due to the influence of weather.

For such reasons, the blade may be damaged. The damage of the blade may include: i) surface roughness caused by icing, pollution, air holes, delamination or the like; ii) mass imbalance caused by water permeation through icing or crack; iii) aerodynamic asymmetry caused by discordance in pitch angle between blades, manufacturing tolerance of aerodynamic profile, deformation of profile during operation or the like; iv) delamination of glass fiber or carbon fiber reinforced plastic structure; and v) surface crack and internal crack.

Conventionally, a fiber Bragg grating (FBG) sensor has been used to monitor the state of a blade. By measuring the strain of the blade through the optical fiber sensor, the load history and vibration of the blade have been measured, and the fatigue damage and lifespan of the blade have been evaluated.

Alternatively, a sensor system using an FBG strain sensor has been constructed for stability monitoring, blade control, load monitoring, fatigue load calculation and the like.

However, such monitoring systems have various problems in that expensive sensors must be used, installation is difficult, and damage occurring inside the blade cannot be sensed.

The wind power generator 1 according to the embodiment of the present invention does not include a separate sensing unit such as an optical sensor, but includes a blade monitoring apparatus which is capable of monitoring an internal/external state of the blade, such as deflection, crack, delamination, or fiber cut, using the property of a material forming the blade, that is, the property of a material having electrical conductivity.

When the skin 141, the spar cap 142, or the shear web 143 which are included in the wind power generator 1 according to the embodiment of the present invention is formed of carbon fiber, the material forming the blade 14 includes a conductive region having electrical conductivity.

At this time, when the above-described types of damages occur inside and outside the material forming the blade 14, the electrical characteristic of the damaged part of the blade may be changed. For example, the resistance of a measurement section may be changed. The change in electrical characteristic of the damaged part may be measured to monitor whether the blade 14 is damaged, that is, the state of the blade 14.

For this operation, the wind power generator 1 according to the embodiment of the present invention includes a measurement unit for measuring the change of electrical characteristic.

As described above, the material forming the blade 14 includes carbon fiber and thus has a conductive region therein.

For example, when the entire spar cap 142 is formed of carbon fiber, the entire region of the spar cap 142 serves as a conductive region. The skin 141 or the shear web 143 may be formed in the same manner.

Within the conductive region, a measurement section may be set. The measurement section may be set by selecting an arbitrary region inside and outside the spar cap 142.

As illustrated in FIG. 2A, the measurement section may be set to a section M1 occupying a part of the spar cap 142 in the longitudinal direction of the spar cap 142. Alternatively, the entire length of the spar cap 142 may be set to the measurement section.

The measurement section may include one section or a plurality of sections. Furthermore, the measurement section may be set along various directions inside and outside the spar cap 142, that is, along the longitudinal direction, the widthwise direction, or the thickness direction of the spar cap 142.

The measurement section may be set inside and outside the skin 141 or the shear web 143. When the skin 141 or the shear web 143 is formed of carbon fiber as described above, the skin 141 or the shear web 143 may include a conductive region therein. Within the conductive region, the measurement section M1 may be set in such a manner as described in the case of the spar cap 142.

Furthermore, as illustrated in FIG. 2B, the measurement section may include measurement sections M2 and M3, each of which is set across two or more members, while including a connection part between the respective members forming the blade 14.

For example, the measurement section may include a measurement section M2 set across the skin 141 and the spar cap 142 with a connection part between the skin 141 and the spar cap 142. When both of the skin 141 and the spar cap 142 are formed of carbon fiber, the conductive region having electrical conductivity may be connected from the skin 141 to the spar cap 142 through the connection part between the skin 141 and the spar cap 142. In this case, the measurement section may be set across the skin 141 and the spar cap 142, while including the connection part between the skin 141 and the spar cap 142, and the change in electrical characteristic of the measurement section M2 may be sensed to check damage in the connection part between the skin 141 and the spar cap 142.

Furthermore, the measurement section may include a measurement section M3 set across the spar cap 142 and the shear web 143 with a connection part between the spar cap 142 and the shear web 143. In this case, damage in the connection part between the spar cap 142 and the shear web 143 may be checked.

Any one of the skin 141, the spar cap 142, and the shear web 143 may be formed of glass fiber instead of carbon fiber. The member formed of glass fiber does not have electrical conductivity. That is, the member is formed of a non-conductive material. The member formed of a non-conductive material may include a conductor 146 formed therein.

For example, when the spar cap 142 illustrated in FIG. 3 is formed of a non-conductive material, the conductor 146 may be formed as a separate member within the spar cap 142, or integrated with the spar cap 142. The conductor 142 serves as a conductive region inside the non-conductive member, and a measurement section may be set within the conductive region, as described above. At this time, the conductor 146 may be formed of carbon fiber as described above, and thus have electrical conductivity.

Furthermore, the skin 141 or the shear web 143 may be set to the non-conductive member. In this case, the conductor 146 may be formed within the skin 141 or the shear web 143 formed of a non-conductive material.

The wind power generator 1 according to the embodiment of the present invention includes a measurement unit 410 to measure the change in electrical characteristic of the measurement section.

As illustrated in FIGS. 2A, 2B and 3, the measurement unit 410 may be electrically connected to both ends of the above-described measurement sections M1, M2, and M3. The method for measuring an electrical characteristic may include a method for measuring resistance, for example.

In order to measure resistance, a voltage or current may be applied to the measurement section, and the measurement unit 410 may measure electrical characteristic values of the measurement sections M1, M2, and M3. The measured electrical characteristic values (hereafter, referred to as measured values) may be transmitted to a determination unit 420 which will be described below.

The measurement unit 410 may be configured to repetitively measure the electrical characteristics of the measurement sections, with a predetermined time interval, such that the state of the blade 14 may be continuously monitored.

The wind power generator 1 according to the embodiment of the present invention may include a blade control apparatus for controlling the blade 14 using the measured values transmitted from the measurement unit 410.

As illustrated in FIG. 4, the blade control apparatus may include the measurement unit 410, the determination unit 420, and a control unit 430. The control unit 430 is included to control one wind power generator, and may be considered as a local control unit which is distinguished from an integrated controller 500 to be described below.

Figure 5:
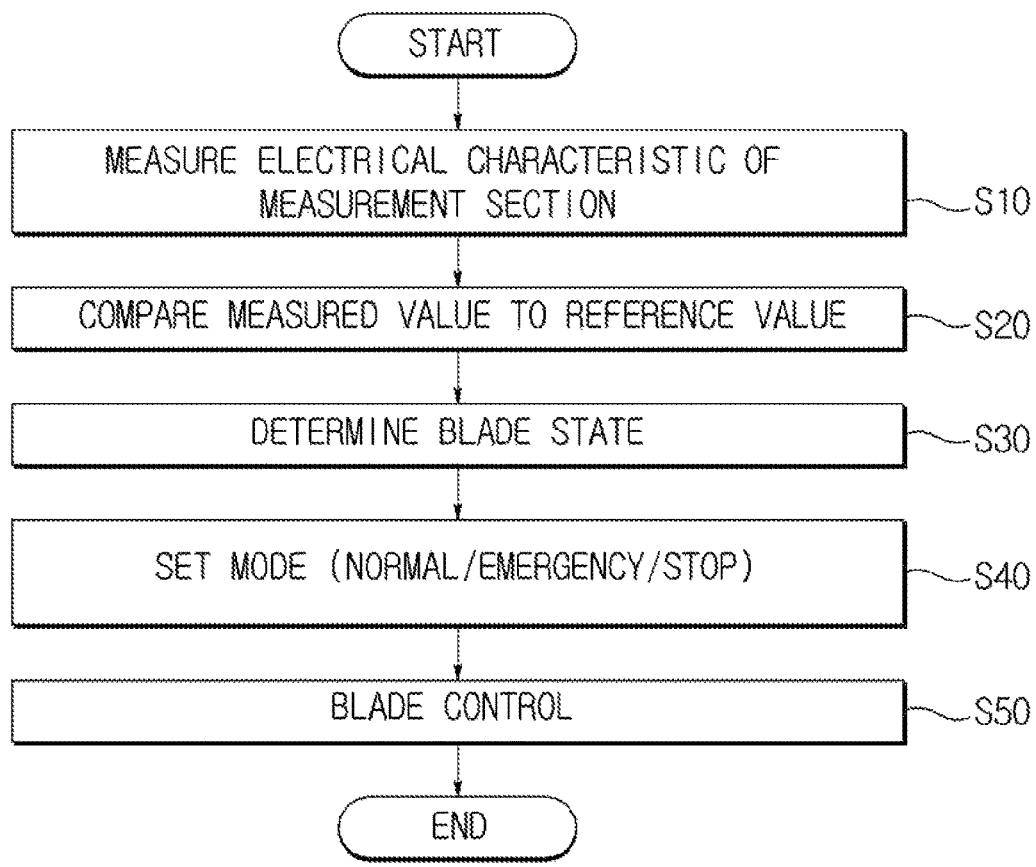
FIG. 5 is a flowchart illustrating a blade control method according to an embodiment of the present invention.

Hereafter, a method for controlling the blade 14 using the blade control apparatus will be described with reference to FIG. 5. FIG. 5 is a flowchart illustrating a blade control method according to an embodiment of the present invention.

As illustrated in FIG. 5, the blade control method includes measuring an electrical characteristic of a measurement section set in a conductive region through the measurement unit 410, at operation S10. At this time, the measurement unit 410 may repetitively measure the electrical characteristic of the measurement section, with a predetermined time interval, such that the state of the blade 14 is continuously monitored.

Then, the determination unit 420 may compare the measured value to a reference value at operation S20, and determine whether the state of the blade 14 is normal or abnormal according to the comparison result, at operation S30.

Then, the control unit 430 may set a mode corresponding to the state determination at operation S40. The mode may be set to any one of a normal mode, an abnormal mode, and a stop mode. According to the set mode, the control unit 430 may control the rotation condition of the blade 14 at operation S50.

Figure 6:
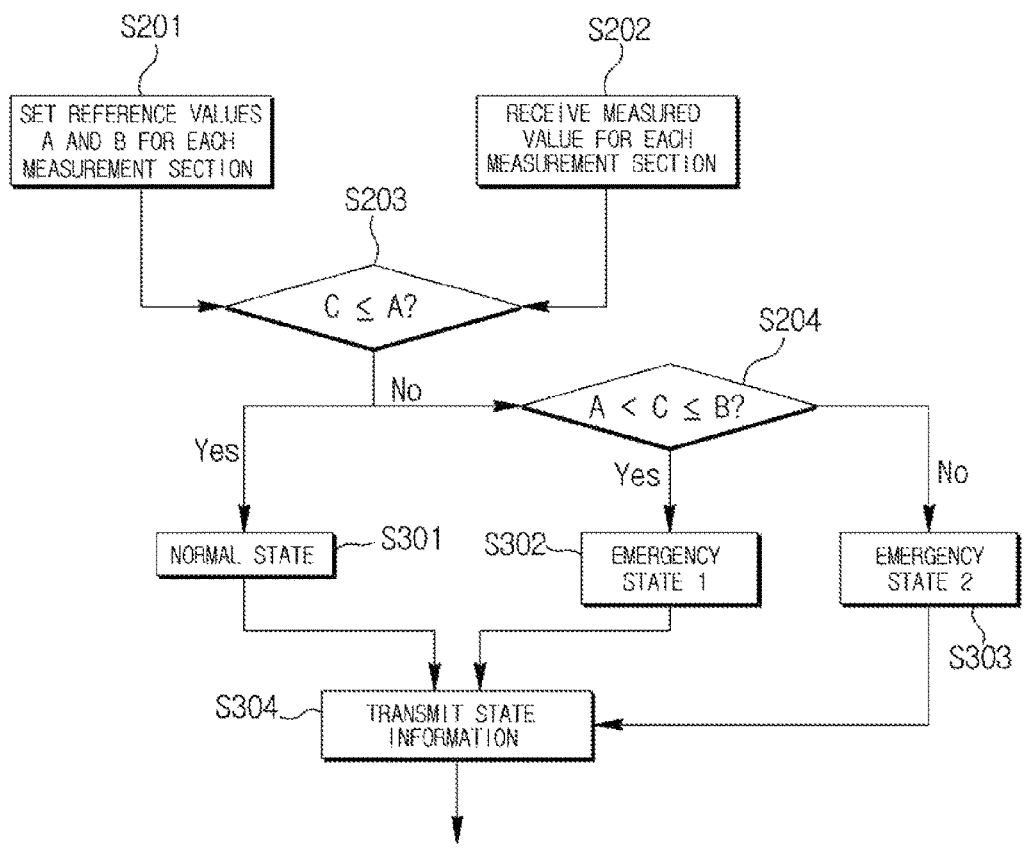
FIG. 6 is an algorithm flowchart of a determination unit of FIG. 4.
Figure 7:
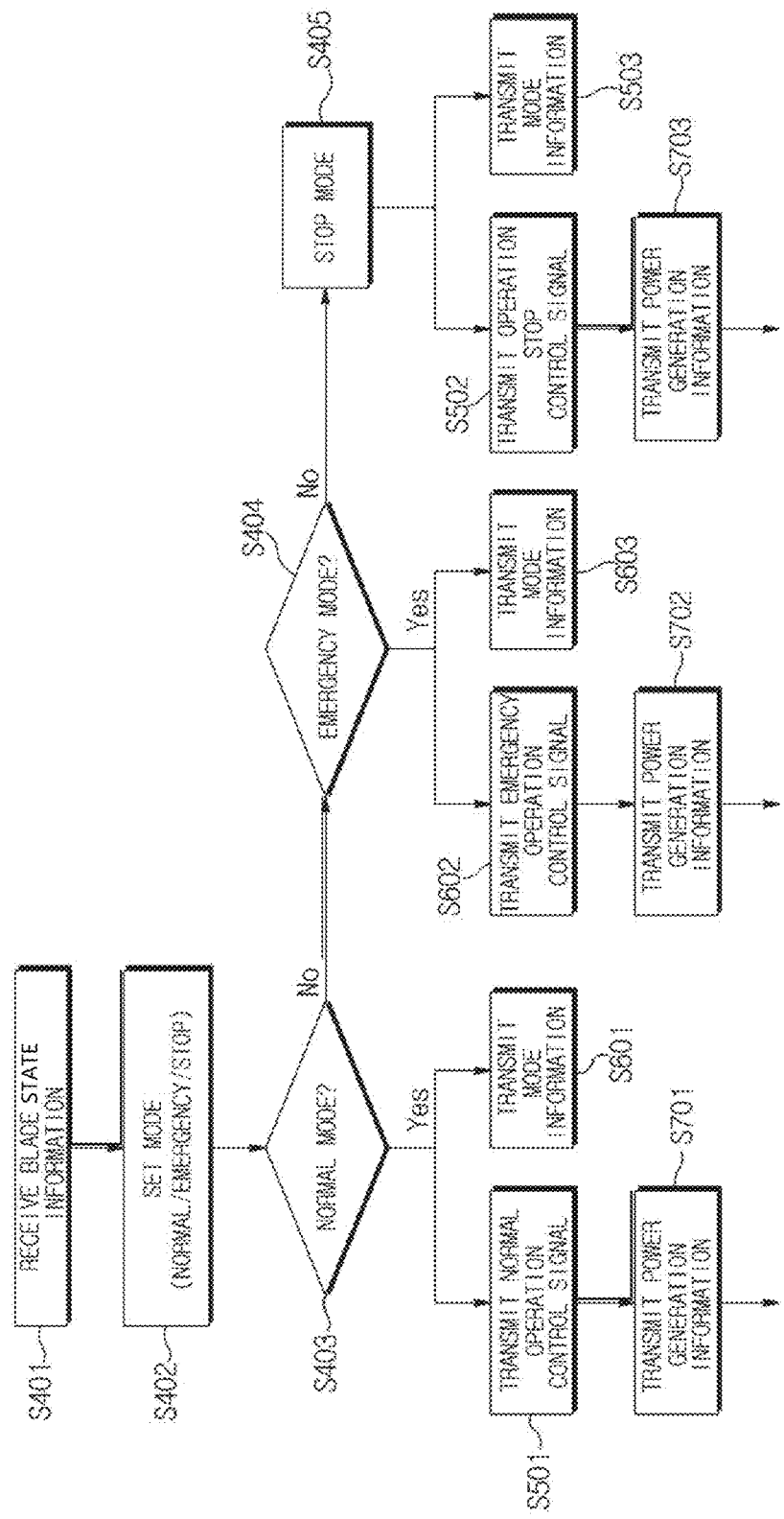
FIG. 7 an algorithm flowchart of a control unit of FIG. 4.

The specific functions of the determination unit 420 and the control unit 430 and the blade control method based on the functions will be described in more detail with reference to FIGS. 6 and 7. FIG. 6 is an algorithm flowchart of the determination unit illustrated in FIG. 4, and FIG. 7 is an algorithm flowchart of the control unit illustrated in FIG. 4.

As illustrated in FIG. 6, the determination unit 420 may previously set a reference value for each measurement section at operation S201. The reference value may include a boundary value A for distinguishing between a normal state and an emergency state. Alternatively, the reference value may include a level value B for determining the level of the emergency state.

The boundary value A or the level value B may be more subdivided. In FIG. 6, the level value B is used as one value for determining the level at which emergency operation control is required and the level at which operation stop control is required. However, the level value B may include a plurality of subdivided values for controlling the blade 14 in response to the level of change in electrical characteristic of the measurement section, that is, the level of the emergency state.

The boundary value A or the level value B may be set to a specific value or a specific range.

The determination unit 420 may receive a measured value C from the measurement unit 410 at operation S202, and compare the measured value C to the reference values A and B at operations S203 and S204. When the measured value C is smaller than or equal to the boundary value A, it may indicate that the change of electrical characteristic is not large. Thus, the determination unit 420 may determine that the state of the blade 14 is normal, at operation S301.

When the measured value C is larger than the boundary value A, the determination unit 420 may determine that the blade 14 is in an emergency state. The emergency state may indicate the case in which deflection, icing, crack, delamination of the stacked structure, or fiber cut occurred in the blade 14. In this case, the rotation condition of the blade 14 needs to be controlled.

At this time, when the measured value C is larger than the boundary value A but smaller than or equal to the level value B, the determination unit 420 may determine that the blade 14 is in an emergency state but the operation stop control is not required, at operation S302. However, when the measured value C is larger than the level value B, it may indicate that the change of electrical characteristic is large. Thus, the determination unit 420 may determine that the damage of the blade 14 is serious and the operation of the blade 14 needs to be stopped, at operation S303.

The determination unit 420 may transmit the determination information on the state of the blade 14 to the control unit 430 at operation S304. The control unit 430 outputs a control signal to optically control the blade using the acquired determination information.

Before the specific control operation of the control unit 430 is described, an optimal control method for the blade will be described as follows.

In order to convert kinetic energy, generated from wind of which the direction and strength are irregularly changed, into mechanical power as much as possible, the pitch and yaw of the blade and the rotation speed of the rotor need to be optimally controlled according to the change in speed and direction of wind.

The optimal control needs to be designed to not only extract the maximum output, but also satisfy a function of minimizing a static load and a dynamic load which are applied to mechanical elements having an influence on the manufacturing cost of the wind power generator.

The control method for the wind power generator may include the following three methods.

The first method is the simplest control method which is known as "Danish concept". This method performs only yaw control following the change of wind direction using an induction generator, when the rotation speed of the rotor is constantly maintained regardless of wind speed and pitch control is not required because a pitch angle is fixed.

This method is designed in such a manner that flow separation called stall occurs on the blade at a rated wind speed or more, and limits an output of a rotor to the rated output of a generator. However, since an axial force directed to a rotating shaft continuously maintains a high value at the rated wind speed or more, a wind power generator using this method inevitably has a heavy and expensive mechanical structure.

The second method is a control method that controls pitch of a blade when the RPM of an induction generator is constant. Specifically, this method controls output by reducing a pitch angle at the rated wind speed or more. In this case, although the wind speed increases, an axial force directed to a rotating shaft may be decreased to significantly reduce a load applied to the mechanical structure.

Third method is the most optimal control method that is mainly employed in recent large-size wind power generators. This method controls the rotation speed of the rotor according to the wind speed, in addition to the pitch and yaw control, and maintains a tip speed ratio to an optimal design value at the rated wind speed or less, thereby maximizing energy extraction. The variable RPM control may be performed through torque control for the generator, and performed through torque and pitch control at the rated wind speed or more.

The yaw control may be applied in the same manner to the wind power generator, regardless of the three control methods, and have a serious influence on energy production. The control algorithm for a yaw apparatus for moving a rotor according to the change of wind direction needs to be designed to obtain the maximum energy production in consideration of the change of wind direction with respect to time.

The control unit 430 may perform the following control process such that the blade is optimally controlled as described above.

As illustrated in FIG. 7, the control unit 430 may receive the state information of the blade 14 from the determination unit 420 at operation S401, and set a mode corresponding to the received information at operation S402. The mode set at operation S402 may include any one of the normal mode, the abnormal mode, and the stop mode.

The control unit 430 may set the mode to the normal mode when the state information received from the determination unit 420 indicates a normal state, at operation S403. When the mode is set to the normal mode, the normal operation control is performed on the rotation condition of the blade 14, at operation S501. The control unit 430 may check power generation based on the normal operation control, and transmit the checked power generation information to the integrated controller 500 to be described below, at operation S701.

When the state information received from the determination unit 420 indicates an emergency state, that is, when the state of the blade 14 is determined to be an emergency state 1 according to the comparison result with the level value B at operation S301 (refer to FIG. 6), the control unit 430 sets the mode to the abnormal mode at operation S404.

When the mode is set to the abnormal mode, the control unit 430 may transmit an emergency operation control signal at operation S602. The emergency operation control signal may include any one of a rotation speed control signal for controlling the rotation speed of the rotor 10 including the blade 14, a pitch control signal for controlling the pitch angle of the blade 14, and a yaw control signal for changing an angle corresponding to the wind direction of the rotor 10.

The rotation speed control signal may be transmitted to a brake unit for controlling the rotation speed of the rotor 10.

The pitch control signal may be transmitted to the pitch controller of the blade 14. Pitch indicates an angle at which the blade 14 is twisted. The pitch angle of the blade 14, controlled through the pitch controller, may be set to 90 degrees in an idling state where the wind power generator generates no power. At this time, the blade 14 is arranged in a direction parallel to the direction in which wind blows, and the angle of attack for the blade 14 may be maintained at zero degrees such that the smallest load is applied to the blade 14.

When the blade 14 is determined to be in an emergency state and thus the mode is set to the abnormal mode, the control unit 430 may transmit a control signal for controlling the pitch controller to control the pitch angle of the blade 14, in order to reduce the load applied to the blade 14.

The yaw control signal may be applied in the same manner. That is, the control unit 430 may transmit a control signal for controlling the yaw controller to perform yaw control. That is, the direction of the blade 14 may be switched to a position at which the rotor 10 is less affected by wind, in order to reduce the load applied to the blade 14.

The control unit 430 may transmit the emergency operation control signal to control the blade 14, at operation S602. Then, the control unit 430 may check the reduction in power generation of the wind power generator 1 according to the emergency operation control, and transmit the checked power generation information to the integrated controller 500, at operation S702.

When the state information received from the determination unit 420 indicates an emergency state, that is, when the state of the blade 14 is determined to be an emergency state 2 according to the comparison result with the level value B at operation S204 (refer to FIG. 6), the control unit 430 may set the mode to the stop mode at operation S405. In this case, the blade 14 needs to be repaired or replaced. Thus, the rotation of the blade 14 needs to be stopped.

When the mode is set to the stop mode, the control unit 430 may transmit an operation stop control signal at operation S502. The operation stop control signal may be transmitted to the brake unit for controlling the rotation speed of the rotor 10, and the rotor 10 may be stopped by the brake unit. Even in this case, the control unit 430 may check the reduction in power generation of the wind power generator 1, and transmit the checked power generation information to the integrated controller 500 at operation S703.

The control unit 430 may perform mode information transmission operations S601, S503, and S603 such that a manager checks the mode information after the mode is set at operation S402. The mode information may be transmitted as a text message to a mobile terminal carried by the manager, for example. Alternatively, the mode information may be transmitted to a management system for managing the wind power generator 1, and then displayed on a display screen of an external terminal of the management system. Alternatively, the mode information may be transmitted as an e-mail to an e-mail account of the manager.

In particular, when the state of the blade 14 is determined to be an emergency state and thus the mode is set to the abnormal mode or the stop mode, the control unit 430 may transmit a control signal for turning on a warning light (not illustrated) or a control signal for controlling a warning sound generator (not illustrated) to generate a warning sound.

Figure 8:
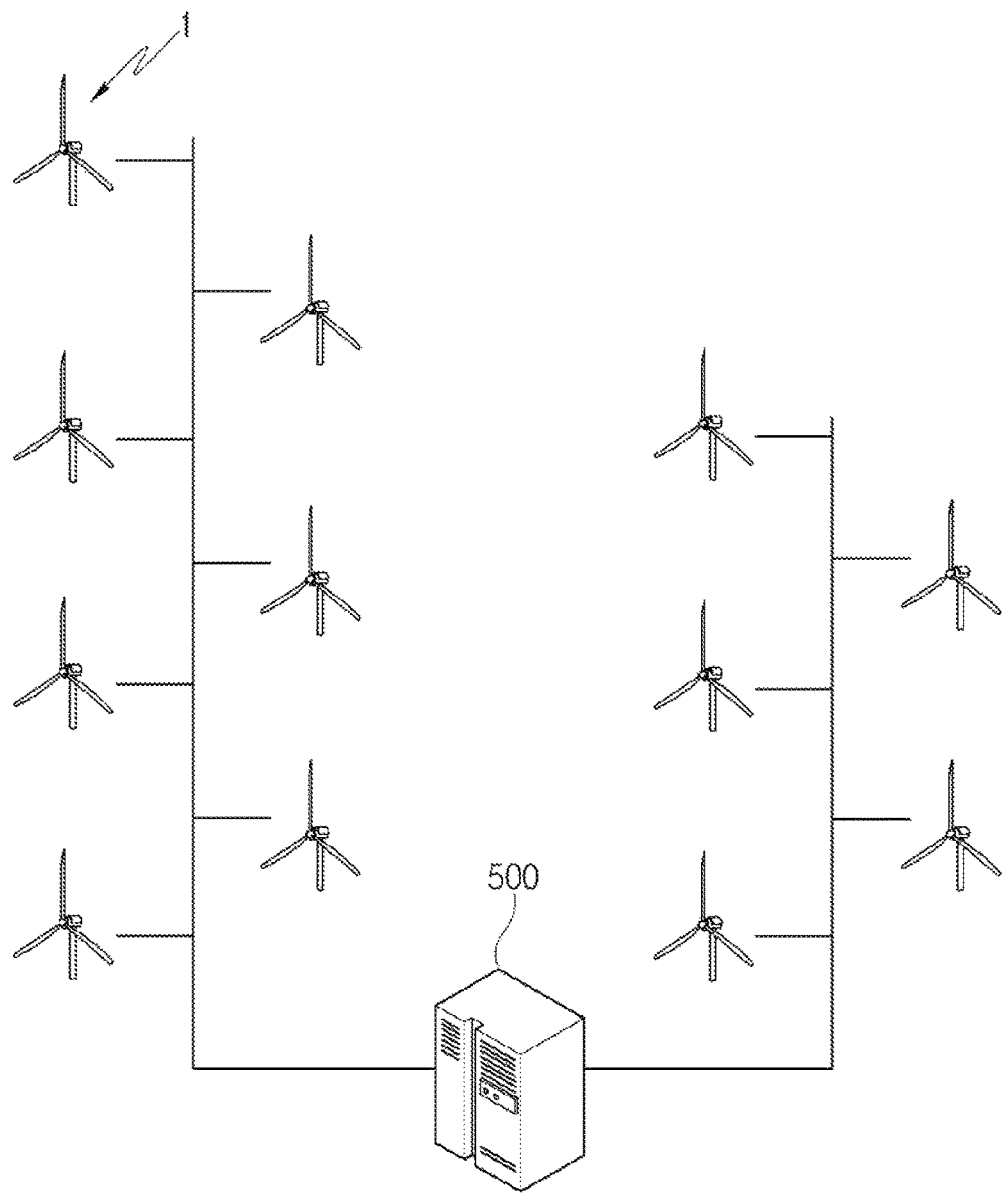
FIG. 8 is a schematic view of a wind power generator.

As illustrated in FIG. 8, the wind power generator 1 according to the embodiment of the present invention may include any one of a plurality of wind power generators included in a wind farm.

The wind farm may be managed through a management system on the ground, for example. The management system may include the integrated controller 500 for integrally controlling the plurality of wind power generators. The integrated controller 500 may communicate with a local control unit and controls a wind power generator which is handled by the local control unit.

The local control unit may continuously transmit information on the power generation of the wind power generator to the integrated controller 500 at operations S701, S702, and S703 (refer to FIG. 7). The integrated controller 500 may analyze the acquired power generation information, and control each of the wind power generators to adjust the output thereof, if necessary. For example, when reduction in power generation of a wind power generator is checked through information transmitted from a local control unit, the integrated controller 500 may transmit a control signal to another local control unit to adjust the output of a wind power generator handled by the local control unit.

According to the embodiments of the present invention, the member forming the blade for a wind power generator may include a conductive region based on the characteristic of the material. In this case, the change in electrical characteristic of a measurement section within the conductive region may be changed to easily check the state of the blade.

Since the member forming the blade functions as a sensor, the state of the blade may be checked even through a separate sensor such as an optical sensor is not provided. Thus, the manufacturing cost may be reduced, and an unnecessary process for installing a sensor may be omitted when the blade is manufactured. Thus, the manufacturing process may be simplified.

Furthermore, the process of checking the state of the blade may include the process of measuring a change of electrical change which occurs in the member forming the blade. Thus, it is possible to check external damage, such as deflection, foreign matters adhering on the blade, or icing, and internal damage, such as crack, delamination, and fiber cut.

Furthermore, the unit for measuring the state of the blade serves as the unit for sensing the change in electrical characteristic of the member forming the blade. Thus, it is possible to reduce the possibility of failure occurrence and easily secure reliability.

While the present invention has been described with respect to the specific embodiments, it will be apparent to those skilled in the art that various changes and modifications may be made without departing from the spirit and scope of the invention as defined in the following claims.

What is claimed is:
1. A wind power generator comprising:
 a blade formed of carbon fiber material and comprising a conductive region having electrical conductivity in the carbon fiber material;
 a detector configured to detect a change in an electrical resistance of a section of the conductive region of the carbon fiber; and
 a determination unit configured to receive the detected change in the electrical resistance that has been transmitted from the detector, compare the detected change in the electrical resistance to a predetermined value, and determine the blade is in a normal state when the detected change is less than or equal to the predetermined value and the blade is in an abnormal state when the detected change is more than the predetermined value,
 wherein the blade comprises a skin, a spar cap, and a shear web,
 the shear web and the spar cap are entirely formed of the carbon material so that the conductive region is formed in the shear web and in the spar cap, and the conductive region encompasses, the shear web, the spar cap, and an interface between the shear web and the spar cap.
2. The wind power generator according to claim 1, wherein the skin is entirely formed of the carbon fiber material, wherein the conductive region is formed to encompass an interface between the spar cap and the skin.

3. The wind power generator according to claim 1, wherein the detector is electrically connected to two locations of the section so as to measure the electrical resistance of the section.

4. The wind power generator according to claim 1, further comprising a control unit configured to set a mode to any one of a normal mode, an abnormal mode, and a stop mode in response to the one of the normal or the abnormal states determined by the determination unit, and control the blade according to the mode.

5. The wind power generator according to claim 4, wherein the control unit transmits any one of a rotation speed control signal, a stop control signal, a pitch control signal, and a yaw control signal for the blade, in response to a level of the abnormal state determined by the determination unit.

6. The wind power generator according to claim 1, wherein the blade further comprises a frame, and wherein the skin tightly covers the frame, the spar cap is coupled to the frame and serves as a stiffener in a longitudinal direction of the blade, and the shear web is coupled to the spar cap and serves as a stiffener in a thickness direction of the blade, and wherein a measurement section is disposed across the spar cap and the shear web, so that the change in electrical resistance is measured at opposite ends of the measurement section that is disposed across the spar cap and the shear web.

7. A blade control apparatus which determines a state of a blade for a wind power generator, the blade formed of carbon fiber material and comprising a conductive region having electrical conductivity in the carbon fiber material, and controls a rotation condition of the blade, the apparatus comprising:
a detector configured to detect a change in an electrical resistance of a section set in the conductive region of the carbon fiber forming the blade,
wherein the blade comprises a skin, a spar cap, and a shear web,
the shear web and the spar cap are entirely formed of the carbon material so that the conductive region is formed in the shear web and in the spar cap, and the conductive region encompasses, the shear web, the spar cap, and an interface between the shear web and the spar cap;
a determination unit configured to receive the detected change in the electrical resistance that has been transmitted from the detector, compare the detected change in the electrical resistance to a predetermined value, and determine the blade is in a normal state when the detected change is less than or equal to the predetermined value and the blade is in an abnormal state when the detected change is more than the predetermined value; and
a control unit configured to set a mode to any one of a normal mode, an abnormal mode, and a stop mode in response to the determined one of the normal or the abnormal state, and control the rotation condition of the blade according to the mode.

8. The blade control apparatus according to claim 7, wherein the section includes one section or a plurality of sections set in the conductive region.

9. The blade control apparatus according to claim 7, wherein the detector repetitively measures the electrical resistance of a measurement section.

10. The blade control apparatus according to claim 7, wherein the control unit transmits any one of a rotation speed control signal, a stop control signal, a pitch control signal, and a yaw control signal for the blade, according to a result determined by the determination unit.

11. A blade control method which measures a state of a blade for a wind power generator, the blade formed of carbon fiber material and comprising a conductive region having electrical conductivity in the carbon fiber material, wherein the blade comprises a skin, a spar cap, and a shear web, and controls a rotation condition of the blade, the method comprising:
measuring an electrical resistance of a measurement section set in the conductive region,
wherein the shear web and the spar cap are entirely formed of the carbon material so that the conductive region is formed in the shear web and in the spar cap, and the conductive region encompasses, the shear web, the spar cap, and an interface between the shear web and the spar cap;
comparing the measured electrical resistance to a reference value and determining whether the blade is in a normal state or an abnormal state based on a result of the comparing,
wherein, the blade is in the normal state when the comparison result is less than or equal to the reference value and the blade is in the abnormal state when the comparison result is more than the reference value;
setting a mode to any one of a normal mode, an abnormal emergency mode, and a stop mode based on a result of the determining of whether the blade is in the normal or the abnormal states; and
controlling the rotation condition of the blade according to the mode.

12. The blade control method according to claim 11, wherein the measuring of the electrical resistance comprises measuring electrical characteristics of a plurality of measurement sections set in the conductive region.

13. The blade control method according to claim 11, wherein the measuring of the electrical resistance comprises repetitively measuring the electrical resistance of the measurement section.

14. The blade control method according to claim 11, wherein the controlling of the rotation condition comprises controlling one or more of rotation speed, pitch, and yaw of the blade in response to a level of the abnormal state determined at the setting of the mode, or stopping the blade.

15. The blade control method according to claim 11, further comprising checking generation quantity of the wind power generator after the controlling of the rotation condition.

16. The blade control method according to claim 15, wherein the wind power generator including the blade is one of a plurality of wind power generators forming a wind farm, and the wind farm includes an integrated controller for controlling the plurality of wind power generators, and the blade control method further comprises transmitting the power generation information to the integrated controller after the checking of a generation quality.

* * * * *